April 28, 1964 C. FISCHER Plant Pat. 2,393
GLADIOLUS PLANT
Filed April 30, 1963
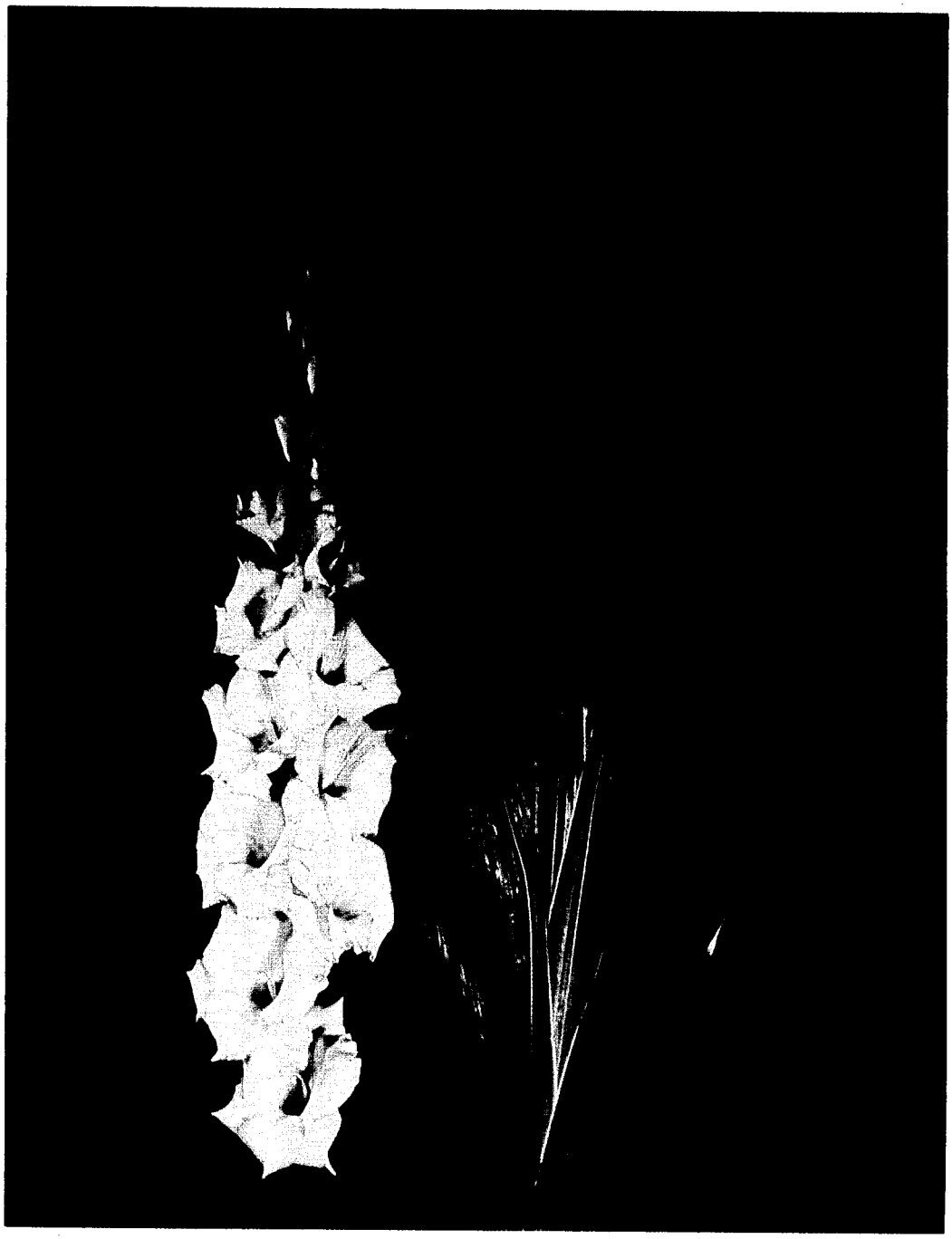
Inventor.
Carl Fischer
By: Robb & Robb
Attorneys.

United States Patent Office

Plant Pat. 2,393
Patented Apr. 28, 1964

2,393
GLADIOLUS PLANT

Carl Fischer, St. Charles, Minn., assignor to Imperial Flowers Limited, Leamington, Ontario, Canada, a corporation of Ontario, Canada Filed Apr. 30, 1963, Ser. No. 277,051
1 Claim. (Cl. Plt.—85)

The present invention relates to a new and distinct variety of gladiolus plant which was originated by me by crossing two gladiolus varieties whose identities are presently unknown by virtue of the fact that my records of this cross and the plant labels were lost during my breeding and testing operations.

As the result of this breeding, I have produced a new and improved gladiolus variety, as evidenced by the following unique combination of characteristics which are outstanding therein and which distinguish it from its parents, as well as from all other varieties of which I am aware:

(1) An extremely vigorous habit of growth;

(2) Consistency of performance and the ability to grow well in Southern climates where the day lengths are short, and particularly in the area of the State of Florida during the wintertime; and (3) A distinctive and attractive Phlox Purple general color tonality of the flowers, with a blur of creamy white deep in the throat of the lip petal, and with a scarlet outline on the reverse of the calyx and at the point where the petals separate.

My new variety resembles the variety known as "Benjamin Britton" (unpatented) more than any other variety, but differs particularly therefrom by having a greater temperature tolerance, with consequent ability to grow better in the State of Florida in the wintertime; produces larger florets; has more florets open at one time; and the flowers have a cleaner color.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike and typical foliage of my new variety, with the flowers in different stages of development ranging from closed buds through partially open buds to fully open buds, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations from cormels.

*Plant*

Growth: Extremely vigorous; average propagator.

Blooming habit: Comes into bloom in about 85 days from large bulbs in the Northern latitudes of the United States.

Stems: Straight and willowy.

*Diameter at base.*—About ⅜ inch.

*Color (at base).*—Rose tinted.

Foliage: Broad and arranged in fan-shaped relation on the plant; individual leaves average about 1¾ inches in width and attain a height of about 35 inches. Color—healthy deep green.

Disease resistance: Unusually resistant to the usual diseases to which gladiolus varieties are normally subject, as determined by comparison with other varieties grown in my fields near St. Charles, Minnesota.

Corms (bulbs): Round; plump; well-husked, with husks having a purplish cast. Color of flesh—Amber Yellow, Plate 505/1.

*Flower*

Spike: Blossom spike averages from 50 inches to 56 inches in height, with flower head averaging about 24 inches long; bears from 18 to 22 buds, with from 6 to 8 buds open at one time.

Bud:

*Size.*—About 3 inches long when opening.

*Opening.*—Opens unusually well from tight buds; from 6 to 8 buds show color at one time.

Flower:

*Arrangement.*—Florets are semi-formally arranged on the stem.

*Size.*—Individual florets average about 5½ inches in diameter, with upper florets being progressively smaller.

*Form.*—Very recurved; plain, but with slight needlepointing at the midribs.

*Keeping qualities.*—Keeps well.

Petals:

*Shape.*—Broad; recurved; some needlepointing.

*Size.*—Upper petals—about 2¼ inches wide. Lip petal—about 1⅝ inches wide.

*Aspect.*—From thin to average substance; smooth surface.

*Fragrance.*—None.

*Color.*—General color effect is Phlox Purple, Plate 632/2, with a tint of Phlox Purple, Plate 632/1 at edges of petals, and throat line being Phlox Purple, Plate 632/1; a creamy white blur deep in the throat of the lip petal, and a scarlet outline on the reverse of the calyx and at the point where the petals separate.

*Reproductive Organs*

Stamens: Color—purple.

Pistil: Color—Phlox Purple, Plate 632/1.

I claim:

A new and distinct variety of gladiolus plant, substantially as herein shown and described, characterized particularly as to novelty by the unique combination of an extremely vigorous habit of growth, consistency of performance and ability to grow well in areas where the day length is short, such as in the State of Florida during the wintertime, and a distinctive and attractive Phlox Purple general color tonality of the flowers, with a blur of creamy white deep in the throat of the lip petal, and with a scarlet outline on the reverse of the calyx and at the point where the petals separate.

No references cited.